United States Patent [19]

Carter

[11] Patent Number: 5,782,408
[45] Date of Patent: Jul. 21, 1998

[54] SCENTED BEDDING ACCESSORY

[75] Inventor: Katharine Carter, 12505 E. 86th St., Indianaoplis, Ind. 46236-8548

[73] Assignees: Katharine Carter; Vida Lorraine Carter, both of Indianapolis, Ind.

[21] Appl. No.: 613,454

[22] Filed: Mar. 1, 1996

[51] Int. Cl.⁶ .................. A24F 25/00; A61L 9/04
[52] U.S. Cl. ................................. 239/34; 5/658
[58] Field of Search ................. 239/34, 36, 145, 239/326; 5/482, 499, 641, 658

[56] References Cited

U.S. PATENT DOCUMENTS

| | | |
|---|---|---|
| 1,617,822 | 2/1927 | O'Leary . |
| 2,615,754 | 10/1952 | Lindenberg . |
| 3,154,798 | 11/1964 | Harris et al. . |
| 3,185,394 | 5/1965 | Farrell . |
| 3,308,488 | 3/1967 | Schoonman .................. 5/499 X |
| 3,372,407 | 3/1968 | Weber III . |
| 4,277,024 | 7/1981 | Spector . |
| 4,283,011 | 8/1981 | Spector . |
| 4,722,477 | 2/1988 | Floyd ........................ 239/36 |
| 4,744,514 | 5/1988 | Gadoua . |
| 4,826,479 | 5/1989 | Burgin et al. .................. 5/641 X |
| 4,874,129 | 10/1989 | DiSapio et al. ................. 239/36 |
| 5,299,335 | 4/1994 | Ivester et al. . |
| 5,423,711 | 6/1995 | Dorland ........................ 450/57 |

FOREIGN PATENT DOCUMENTS 2183479   6/1987   United Kingdom ............. 239/36

*Primary Examiner*—Andres Kashnikow
*Assistant Examiner*—Robin O. Evans
*Attorney, Agent, or Firm*—Locke Reynolds

[57] ABSTRACT

A bedding accessory including a scented fabric strip is disclosed for removable attachment to bedding having a top surface and a lower surface such as a mattress, futon, pad, and the like. A flexible, generally rectangular sheet is formed of a smooth, soft, thin, sturdy and rip and tear resistant material, such as an airlaid non-woven fabric, and is charged with a scented material. A plurality of attachment strips with self-sticking adhesive disposed on opposing surfaces are mounted to the sheet, whereby the sheet may be disposed across the top surface and removably mounted to the lower surface.

13 Claims, 3 Drawing Sheets

SCENTED BEDDING ACCESSORY

BACKGROUND OF THE INVENTION

1. Field of the Invention

This invention relates generally to accessories to be used with bedding, and particularly relates to a bedding accessory which can be used to provide a pleasant scent in and around bedding.

2. Description of the Prior Art

There are presently available a number of devices that may be utilized to provide a selected chemical substance in airborne form proximate to bedding. One such available device, described in U.S. Pat. No. 3,154,798, includes a mattress having a zippered side-mounted pocket with a plurality of ventilators for disbursing a germicide. Further, in U.S. Pat. No. 3,372,407, a mattress is disclosed having a plurality of scent disbursing devices disposed through side walls of the mattress. In addition, there are presently available a number of pillows capable of releasing a scent, such as described in U.S. Pat. Nos. 1,617,822 and 5,299,335, where a longitudinal opening or slot has been formed in the pillow to contain a removable insert.

Despite the availability of such devices, there exists a need in the art for a bedding accessory that is capable of releasing a pleasant scent in and near a wide variety of existing bedding and does not require a specially constructed mattress, pillow, or similar, yet is inexpensive to produce and may be rapidly and easily used and replaced.

SUMMARY OF THE INVENTION

In order to aid in the understanding of the present invention, it can be stated in essentially summary form that it is directed to a bedding accessory including a scented fabric strip capable of removable attachment to existing bedding.

More specifically, the present invention is directed to a scented bedding accessory capable of removable attachment to bedding having a top surface and a lower surface. The lower surface may be formed by the sides and bottom of bedding such as a mattress, although the variety of bedding contemplated for use with the present invention also includes futons, pads, and the like. The scented bedding accessory includes a flexible, generally rectangular sheet having a sheet bottom surface and a sheet top surface, and is formed of a fabric selected to be smooth, soft, and thin, yet relatively sturdy and resistant to ripping and tearing. The sheet is charged with a scented material which may be selected from any of numerous available fragrances and applied to the sheet by methods including the spraying of liquids. Further, the sheet may be formed to have a variety of configurations in addition to generally rectangular, with the dimensions chosen so that the sheet is capable of being disposed across the top surface and removably attached to the lower surface of the bedding. A plurality of attachment strips, each having a strip first surface and an opposing strip second surface are provided. In addition, a first self-sticking adhesive layer is disposed on each of the strip first surfaces, whereby each of the attachment strips may be mounted to the sheet by disposing the strip first surfaces proximate to the sheet bottom surface with the first self-sticking adhesive layer sandwiched therebetween so that at least one of the attachment strips is disposed proximate to each corner defined by the sheet. A second self-sticking adhesive layer is disposed on each of the strip second surfaces. The attachment strips, and the first and second self-sticking adhesive layers may be formed as unit.

Using the attachment strips, a portion of the sheet may be removably attached to the lower surface of the bedding. This removable attachment is accomplished by placing the second self-sticking adhesive layer in contact with the lower surface of the bedding with a portion of the sheet bottom surface positioned across the top surface of the bedding.

Prior to use, the present invention may be stored in a folded configuration, with release paper may be provided for contact with the second self-sticking adhesive layers of the attachment strips. In this way, the sheet may be easily unfolded, and spread out across the bedding so that a portion of the sheet bottom surface contacts the top surface of the bedding. The dimensions of the sheet are chosen so that the attachment strips are situated for removable coupling to the lower surface. In one aspect of the present invention, the dimensions of the sheet may be selected so that the attachment strips are disposed for removable coupling to that portion of the lower surface formed by the sides of the bedding. Alternatively, the dimensions of the sheet may be selected so that the attachment strips are disposed for removable coupling to that portion of the lower surface formed by the bottom of the bedding. After the sheet is disposed as desired with respect to the bedding, the release paper may be removed and the attachment strips pressed onto the bedding, whereby the sheet is removably attached to the bedding at the lower surface. Further, items such as sheets, blankets and the like may then be disposed over the bedding and the present invention in the customary manner.

In use, scent from the present invention diffuses throughout the bedding material and surrounding area. Also, body heat from bedding occupants may serve to increase the rate of scent diffusion. After a number of days, a significant portion of the scent will have been disbursed, and the sheet and the attachment strips may be removed from the bedding and appropriately discarded. Thereafter another sheet may be attached to the bedding as previously described.

It is an object of the present invention to provide a scented fabric strip that is capable of removable attachment to bedding.

It is another object of the present invention to provide a scented fabric strip that is formed of a fabric that is thin, smooth, and soft, yet is relatively sturdy and resistant to ripping and tearing.

It is another object of the present invention to provide a scented fabric strip that may be easily attached to and removed from bedding.

It is yet another object of the present invention to provide a scented fabric strip that is inexpensive to produce and formed of a minimum number of components.

Further objects and advantages of the present invention will be apparent from a study of the following portion of the specification, the claims, and the attached drawings.

DESCRIPTION OF THE PREFERRED EMBODIMENT

The following portion of the specification, taken in conjunction with the drawings, sets forth the preferred embodiment of the present invention. The embodiment of the invention disclosed herein is the best mode contemplated by the inventor for carrying out the invention in a commercial environment, although it should be understood that various modifications can be accomplished within the parameters of the present invention.

Figure 1:
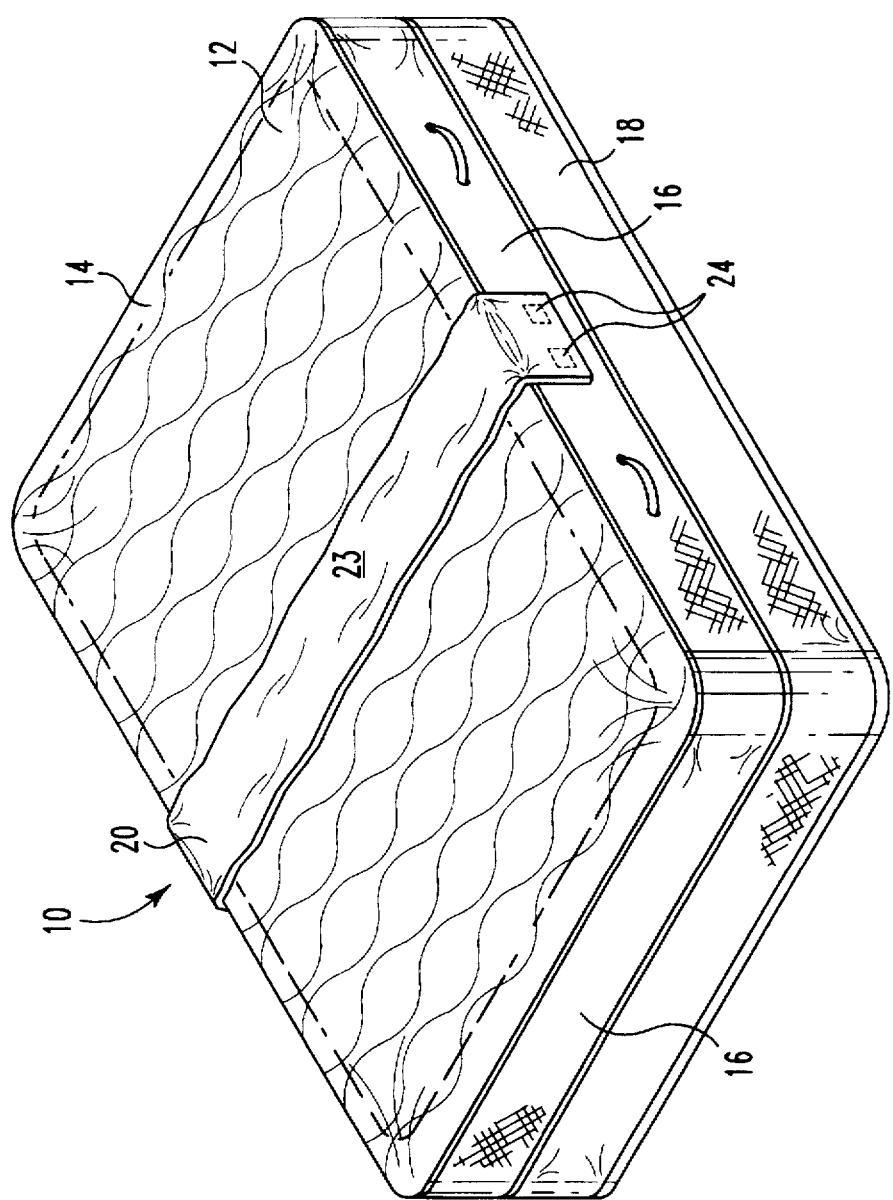
FIG. 1 is a perspective view of a scented bedding accessory representing the present invention depicted as mounted to the sides of a mattress.

Referring now to the drawings for a detailed description of the present invention, reference is first made to FIG. 1, generally depicting by the reference numeral 10 a scented bedding accessory of the present invention disposed in attachment with mattress 12 having top surface 14 and lower surface 16. Lower surface 16 may be formed by the sides and bottom of mattress 12, which may be disposed upon box spring 18. It will be understood that the scented bedding accessory of the present invention may be used in conjunction with a variety of bedding in addition to mattresses, including futons, pads, and the like. The scented bedding accessory of the present invention includes flexible, generally rectangular sheet 20 having sheet bottom surface 22 and sheet top surface 23. Sheet 20 may be formed of a fabric, which may be selected to be smooth, soft, and thin, yet relatively sturdy and resistant to ripping and tearing, for instance, the airlaid non-woven fabric sold as product number 185 of James River Corporation. Sheet 20 is charged with a scented material which may be selected from any of numerous available fragrances. The scented material may be applied to sheet 20 by methods including liquid spraying. Further, sheet 20 may be formed to have a variety of configurations in addition to generally rectangular, with the dimensions of sheet 20 chosen so that sheet 20 is capable of removable attachment to lower surface 16 as will be described.

Figure 2:
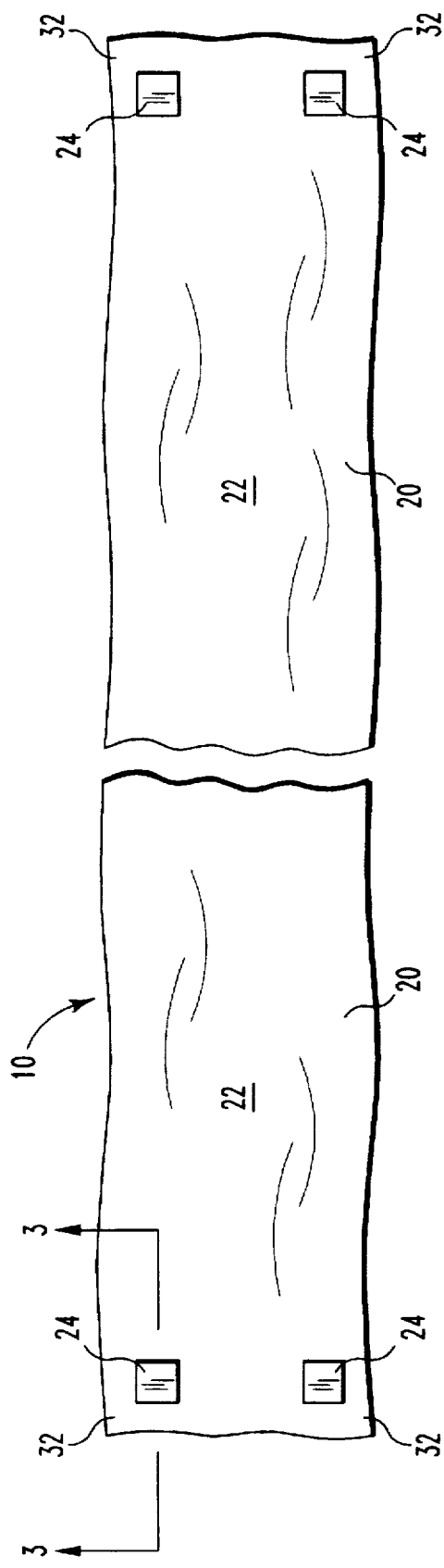
FIG. 2 is an enlarged bottom plan view of a scented bedding accessory representing the present invention.
Figure 3:
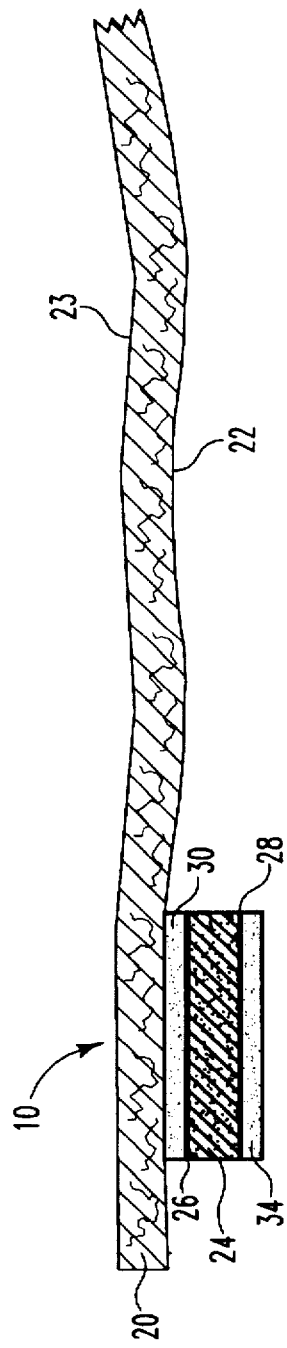
FIG. 3 is a detail cross-section view of a scented bedding accessory representing the present invention, taken along line 3—3 of FIG. 2.

As depicted in FIGS. 1-3, plurality of attachment strips 24, each having strip first surface 26 and opposing strip second surface 28 are provided. In addition, first self-sticking adhesive layer 30 is disposed on each of strip first surfaces 26, whereby each of attachment strips 24 may be mounted to sheet 20 by disposing strip first surfaces 26 proximate to sheet bottom surface 22 with first self-sticking adhesive layer 30 sandwiched therebetween so that at least one of attachment strips 24 is disposed proximate to each corner 32 defined by sheet 20. Second self-sticking adhesive layer 34 is disposed on each of strip second surfaces 28. A portion of sheet 20 may be removably attached to lower surface 16 by disposing strip second surfaces 28 proximate to lower surface 16 with each second self-sticking adhesive layer 34 sandwiched between a strip second surface 28 and lower surface 16 so that each second self-sticking adhesive layer 34 contacts lower surface 16 and a portion of sheet bottom surface 22 is disposed across top surface 14 of mattress 12. Attachment strips 24, and first and second self-sticking adhesive layers 30 and 34 may be formed as unit, such as the product known as Removable Mounting Squares, catalog number 108, sold under the Scotch brand of the 3M Corporation.

Figure 4:
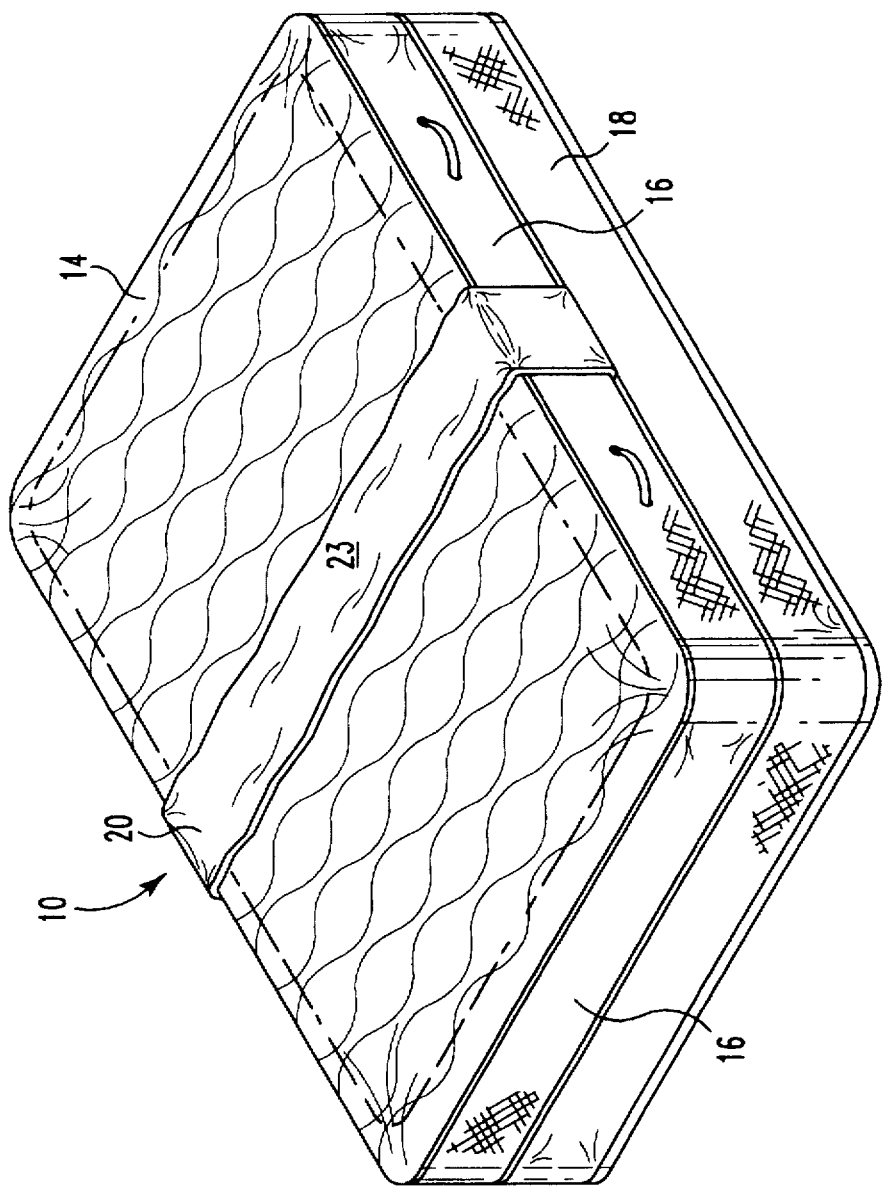
FIG. 4 is a perspective view of a scented bedding accessory representing the present invention depicted as mounted to the bottom of a mattress.

Prior to use, it is contemplated that the present invention may be stored in a folded configuration, with release paper, not shown, provided for contact with second self-sticking adhesive layers 34 of attachment strips 24 before use of the present invention. In this way, sheet 20 of the present invention may be easily unfolded, and spread out across bedding, such as is depicted in FIG. 1 with respect to mattress 12, with a portion of sheet bottom surface 22 disposed in contact with top surface 14 of mattress 12. The dimensions of sheet 20 are chosen so that attachment strips 24 are situated for contact with lower surface 16. As shown in FIG. 1, the dimensions of sheet 20 may be selected so that attachment strips 24 are disposed for removable coupling to that portion of lower surface 16 formed by the sides of the bedding, such as the sides of mattress 12. Alternatively, as illustrated in FIG. 4, the dimensions of sheet 20 may be selected so that attachment strips 24 are disposed for removable coupling to that portion of lower surface 16 formed by the bottom of the bedding, such as the bottom of mattress 12. After sheet 20 is disposed as desired with respect to bedding, such as mattress 12, the release paper may be removed and attachment strips 24 pressed onto mattress 12, whereby sheet 20 is removably attached to mattress 12. Further, items such as sheets, blankets and the like may then be disposed over mattress 12 and the present invention in the customary manner.

In use, scent from the present invention diffuses throughout the bedding material and surrounding area. Also, body heat from bedding occupants may serve to increase the rate of scent diffusion. After a number of days, a significant portion of the scent will have been disbursed, and sheet 20 and attachment strips 24 may be removed as a single unit from the bedding and appropriately discarded. Thereafter, another sheet 20 may be installed as previously described.

The present invention having been described in its preferred embodiment, it is clear that the present invention is susceptible to numerous modifications and embodiments within the ability of those skilled in the art and without the exercise of the inventive faculty. Accordingly, the scope of the present invention is defined as set forth by the scope of the following claims.

What is claimed is:

1. An accessory attachable to bedding having a top surface and a lower surface, comprising:

a thin flexible sheet having a sheet surface; a scented material disposed throughout the sheet;

means for removably attaching a portion of the sheet to the lower surface so that a portion of the sheet surface is disposed to contact the top surface, and the sheet partially surrounds the bedding, wherein the means for removably attaching a portion of the sheet to the lower surface comprises a plurality of couplers attached to the sheet surface and adapted for demountable coupling to the lower surface, and wherein each of the couplers comprises:

an attachment strip having a strip first surface and an opposing strip second surface;

means for attaching the strip first surface to the sheet surface; and means for demountably coupling the strip second surface to the lower surface.

2. The accessory of claim 1 wherein the sheet is generally rectangular and capable of extending substantially across the top surface.

3. The accessory of claim 1 wherein the sheet is formed of a fabric.

4. The accessory of claim 3 wherein the fabric is an airlaid non-woven fabric.

5. An accessory attachable to bedding having a top surface and a lower surface, comprising:

a thin flexible sheet having a sheet surface;

a scented material disposed throughout the sheet; and a plurality of attachment strips. each having a strip first surface and an opposing strip second surface;

a first adhesive layer disposed on each of the strip first surfaces whereby the attachment strips may be mounted to the sheet by disposing the strip first surfaces proximate to the sheet surface with the first adhesive layer disposed therebetween; and a second adhesive layer disposed on each of the strip second surfaces whereby the sheet may be removably attached to the lower surface of the bedding by disposing the strip second surfaces proximate to the lower surface with the second adhesive layer disposed therebetween so that a portion of the sheet surface contacts the top surface and the sheet partially surrounds the bedding.

6. The accessory of claim 5 wherein the sheet is formed of a fabric.

7. The accessory of claim 6 wherein the fabric is an airlaid non-woven fabric.

8. The accessory of claim 5 wherein the sheet is generally rectangular and capable of extending substantially across the top surface.

9. The accessory of claim 8 wherein at least one of the attachment strips is disposed proximate to each corner defined by the sheet.

10. The accessory of claim 5 wherein the first and second adhesive layers are formed of a self-sticking adhesive.

11. An accessory attachable to a mattress having a top surface and a lower surface, comprising:

a thin flexible generally rectangular sheet formed of a fabric and having a sheet surface;

a scented material disposed throughout the sheet;

a plurality of attachment strips. each having a strip first surface and an opposing strip second surface;

a first self-sticking adhesive layer disposed on each of the strip first surfaces whereby the attachment strips may be mounted to the sheet by disposing the strip first surfaces proximate to the sheet surface with the first self-sticking adhesive layer disposed therebetween so that at least one of the attachment strips is proximate to each corner defined by the sheet; and a second self-sticking adhesive layer disposed on each of the strip second surfaces whereby the sheet may be removably attached to the lower surface of the bedding by disposing the strip second surfaces proximate to the lower surface with the second self-sticking adhesive layer disposed therebetween so that a portion of the sheet surface contacts the top surface and the sheet partially surrounds the bedding.

12. The accessory of claim 11 wherein the sheet is formed of an airlaid non-woven fabric and is capable of extending substantially across the top surface.

13. The accessory of claim 12 wherein at least one of the attachment strips is disposed proximate to each corner defined by the sheet.

* * * * *